United States Patent [19]

Hsu

[11] 4,082,428
[45] Apr. 4, 1978

[54] LIQUID CRYSTAL COMPOSITION AND METHOD

[75] Inventor: Ying-Yen Hsu, Mountain View, Calif.

[73] Assignee: Suncrux Incorporated, Cupertino, Calif.

[21] Appl. No.: 710,698

[22] Filed: Aug. 2, 1976

Related U.S. Application Data

[63] Continuation-in-part of Ser. No. 629,396, Nov. 6, 1975, abandoned.

[51] Int. Cl.² .......................... C09K 3/34; G02F 1/13
[52] U.S. Cl. .................................... 350/350; 252/299;
 252/408; 260/463; 260/465 D; 560/19; 560/55
[58] Field of Search ................ 252/299, 408;
 350/160 LC

[56] References Cited

U.S. PATENT DOCUMENTS

| 3,836,478 | 9/1974  | Green et al. .................. 252/299 |
| 3,876,286 | 4/1975  | Deutscher et al. ............ 252/299 |
| 3,915,883 | 10/1975 | VanMeter et al. ............ 252/299 |
| 3,923,857 | 12/1975 | Boller et al. .................. 252/299 |
| 3,953,491 | 4/1976  | Steinstrasser et al. ........ 252/299 |
| 3,975,286 | 8/1976  | Oh .................................. 252/299 |
| 3,981,817 | 9/1976  | Boller et al. .................. 252/299 |
| 3,984,344 | 10/1976 | Cole, Jr. ........................ 252/299 |
| 4,000,084 | 12/1976 | Hsieh et al. ................... 252/299 |
| 4,001,137 | 1/1977  | Steinstrasser ................. 252/299 |
| 4,011,173 | 3/1977  | Steinstrasser ................. 252/299 |

FOREIGN PATENT DOCUMENTS

| 49-88,791 | 8/1974  | Japan ............................. 252/299 |
| 2,459,533 | 7/1975  | Germany ....................... 252/299 |
| 2,538,865 | 3/1976  | Germany ....................... 252/299 |
| 2,321,632 | 11/1974 | Germany ....................... 252/299 |
| 2,447,098 | 10/1975 | Germany ....................... 252/299 |

OTHER PUBLICATIONS

Klanderman, B. H., et al., J. Am. Chem. Soc., vol. 97, No. 6, pp. 1585-1586 (Mar. 19, 1975).
Gray, G. W., et al. Liquid Crystals & Plastic Crystals, vol. 1, John Wiley & Sons, Inc., N. Y., pp. 104, 142-143 (1/6/74).

Primary Examiner—Richard E. Schafer
Assistant Examiner—T. S. Gron
Attorney, Agent, or Firm—Flehr, Hohbach, Test, Albritton & Herbert

[57] ABSTRACT

An optically active chiral nematic compound of the general formula:

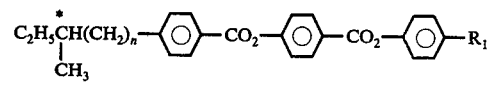

wherein $n$ varies from 1-5, and $R_1$ is a radical selected from the group consisting of an n-alkyl group, an n-alkoxy group, an n-acyloxy group, an n-alkyl carbonato group, a cyano group, and a nitro group. Where $R_1$ contains an alkyl group, it includes from 1 to 8 carbon atoms. The above compound comprises an amount of 0.2 to 2 weight percent in a mixed ester liquid crystal composition with a nematic temperature range of at least 0° to 50° C, said chiral and mixed ester compositions being miscible in each other. A nematic mixed ester liquid crystal composition comprising (a) a mixture of specific alkylphenyl benzoates and (b) a mixture of cyanophenyl benzoates. All of the foregoing compositions being useful as liquid crystals for electro-optical display devices and the like.

19 Claims, 4 Drawing Figures

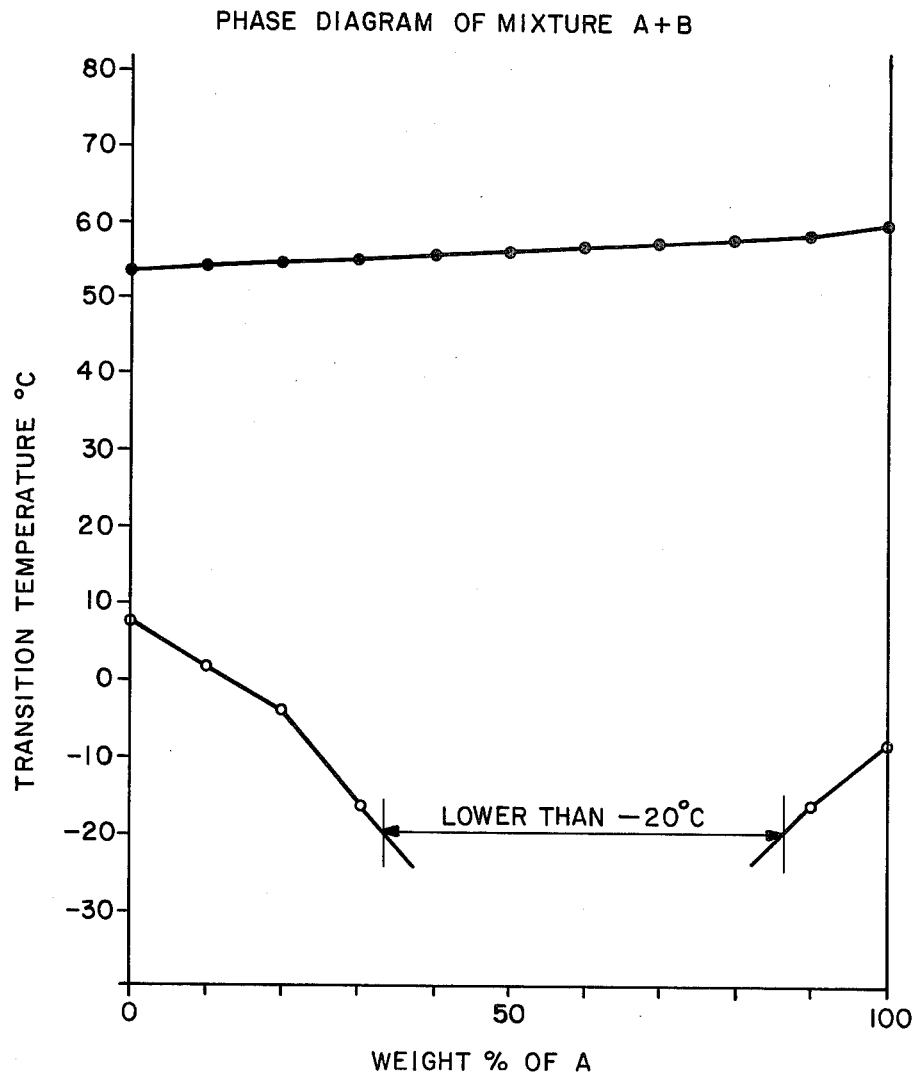
FIG.—1

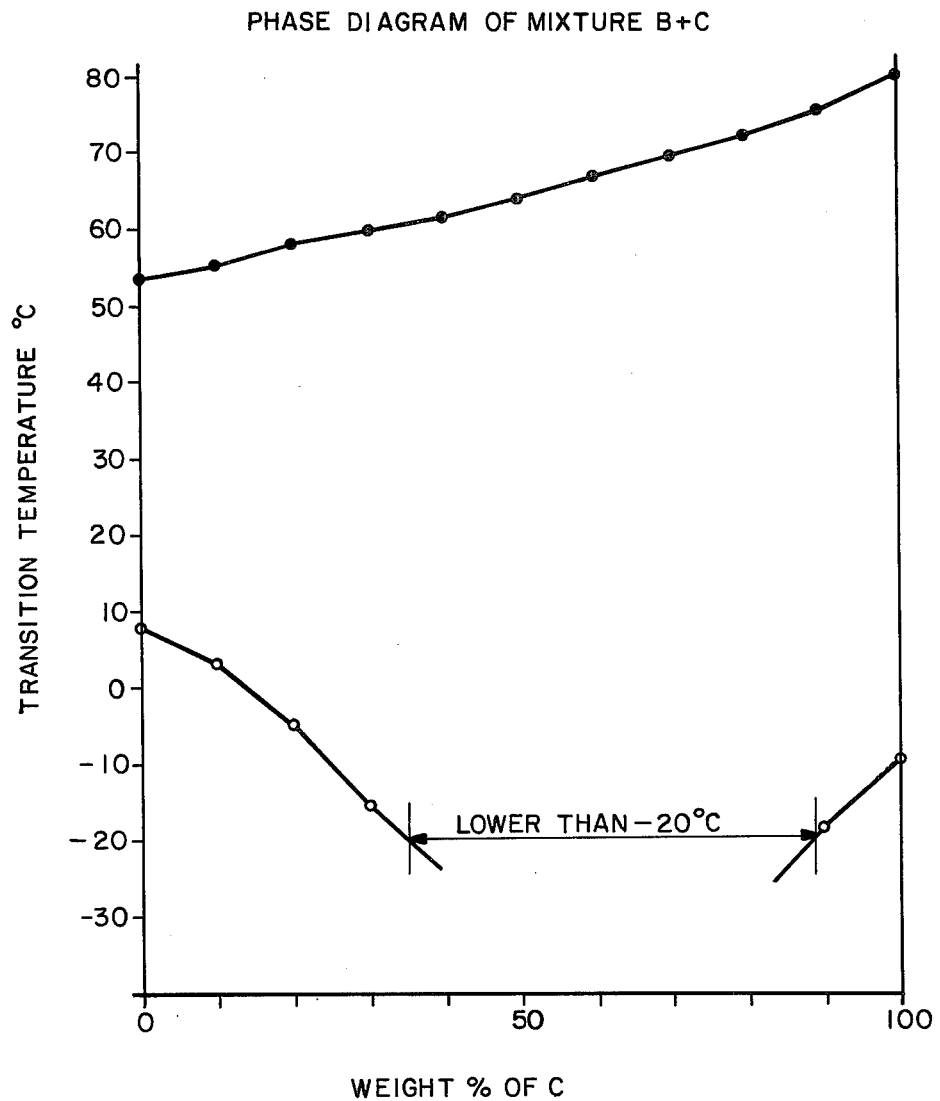
FIG.—2

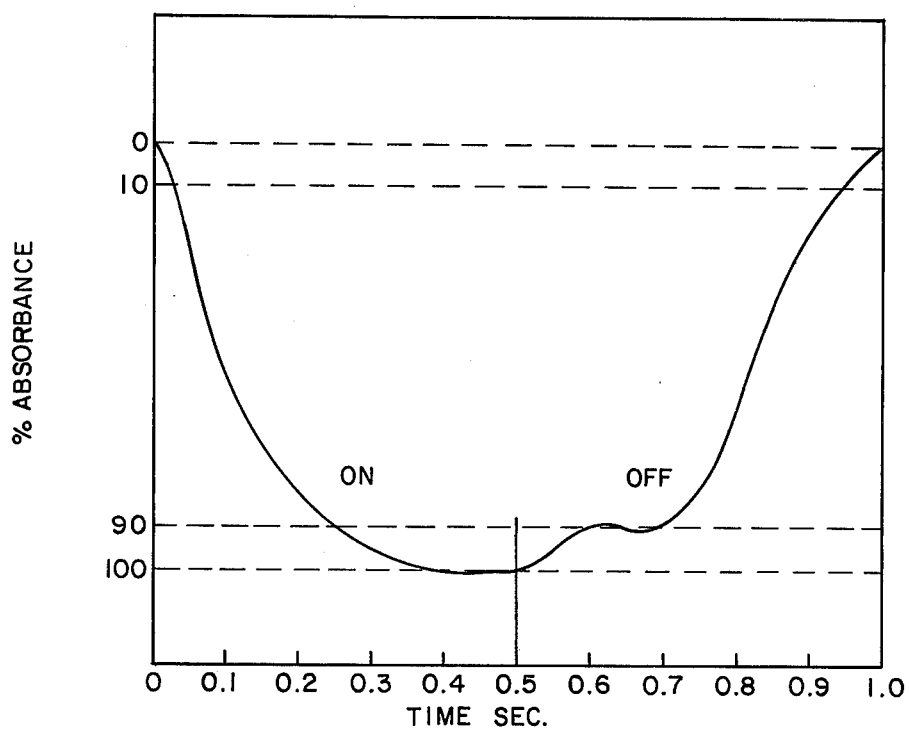
FIG.—3  RESPONSE TIME CURVE
DISPLAY WITHOUT DOPANT OF TABLE XI
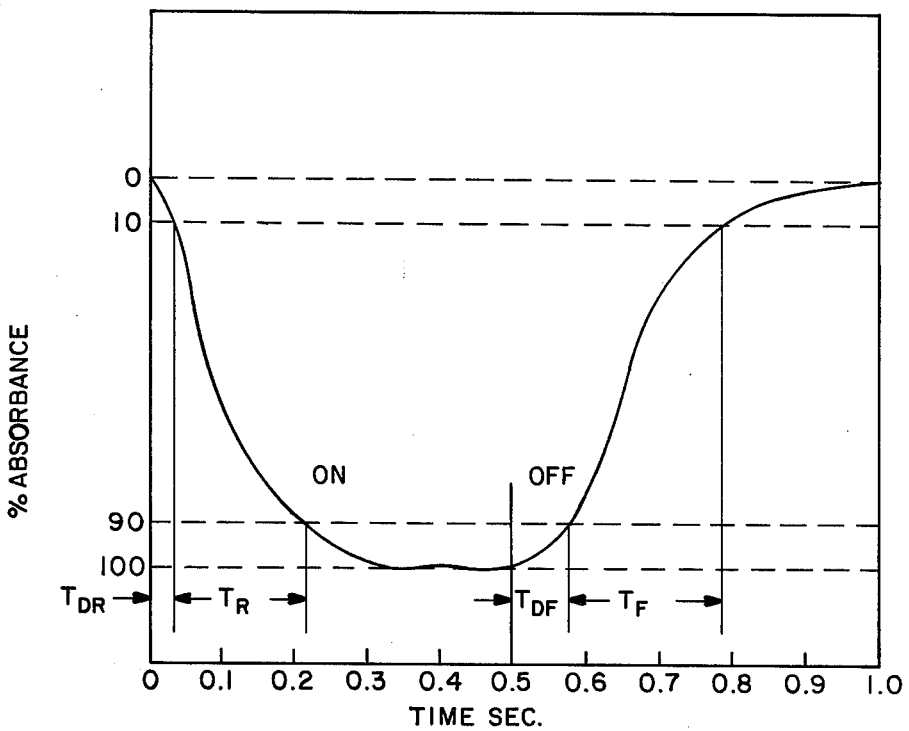
FIG.—4  RESPONSE TIME CURVE
DISPLAY WITH DOPANT (n=1, $R_1=C_1$) OF TABLE XI

LIQUID CRYSTAL COMPOSITION AND METHOD

CROSS-REFERENCE TO RELATED APPLICATION

This is a continuation-in-part of my co-pending application Ser. No. 629,396, filed Nov. 6, 1975, now abandoned.

BACKGROUND OF THE INVENTION

The liquid crystals used in the field effect liquid crystal display are of the nematic type with positive dielectric anisotropy. Such materials are placed in a thin film between transparent electrodes in the form of a 90° twist from the inner surface on one electrode to the inner surface on the other electrode. When an electric field is applied, the liquid crystals align themselves with the field. As is well known, this characteristic enables the liquid crystal to either block or transmit light in a display having polarized end plates depending upon the relative polarization of the plates.

One system employed as the liquid crystal in a twist nematic display is the Schiff base system of $$C_3H_7-\langle O \rangle-CH=N-\langle O \rangle-CN \text{ and}$$

$$C_6H_{13}-\langle O \rangle-CH=N-\langle O \rangle-CN.$$

Schiff base systems are not stable in the presence of water which attacks the —CH=N— link breaking the molecule into two starting materials. The display degradation appears as a decrease in operating temperature range, a significant power increase, and finally a blacking out of the display. Thus, Schiff base materials must be processed in an inert atmosphere and the assembled display must have a true hermetic seal.

Another disadvantage of a Schiff base material is that it is sensitive to ultra-violet light. Degradation from this source is manifest in an increase in power consumption. Because of the aforementioned disadvantages, other compositions have been tested to replace the Schiff base materials in such displays.

Recently, liquid crystal systems of the mixed ester type have been developed for use in a field effect display. These systems are preferable to the aforementioned Schiff base ones because they are more stable in the presence of water or ultra-violet light. A twist characteristic is imposed by placing the liquid crystal between the inner surface of two electrodes which have been treated to impart surfaces aligned at 90° to each other. The liquid crystal adjacent to such surfaces orient along the 90° alignment and form a natural twist.

One type display of mixed ester liquid crystal is set forth in a paper entitled "Design Considerations for Positive Dielectric Nematic Mixtures Suitable for Display Applications", presented at the Fifth International Liquid Crystal Conference — Stockholm, Sweden, June 17-21, 1974. That paper discloses a mixture of six different p,p'-phenyl benzoate esters of the following formula:

Table I p,p'-Phenyl Benzoate Esters

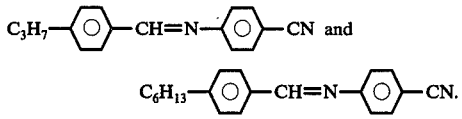

| Compound | X | Y |
| --- | --- | --- |
| I | $CH_3O-$ | $n-C_5H_{11}-$ |
| II | $n-C_5H_{11}O-$ | $n-C_5H_{11}-$ |
| III | $n-C_5H_{11}-$ | CN |
| IV | $n-C_7H_{15}-$ | " |
| V | $n-C_5H_{11}O-$ | " |
| VI | $n-C_7H_{15}O-$ | " |

The above paper states the composition has a nematic temperature range of from −7° to 58°.

Two requirements of a liquid crystal composition are a nematic temperature range of sufficient breadth for operation in varying climates, e.g., at least from 0° C to 50° C and a positive anisotropy or $\Delta\epsilon > 0$. The cyano materials in the above table contribute to positive anisotropy while the alkyl benzoates contribute to a wide temperature range.

A major problem of liquid crystal ester mixtures is that they have a relatively slow response time to return to the chiral state after the electric field is removed (termed "decay time"). The decay time is particularly slow at relatively high voltages, e.g., 3 volts or more.

SUMMARY OF THE INVENTION AND OBJECTS

It is an object of the invention to provide a novel mixed ester composition with a temperature range suitable for use in a liquid crystal display.

It is another object of the invention to provide a novel chiral nematic compound and a method for forming the same which compound is suitable for use as a dopant in a mixed ester display which, in relatively small quantities, dramatically reduces the response time of the mixed esters in a field effect liquid crystal display by imparting a predetermined pitch to the mixed esters.

It is another object of the invention to provide a nematic liquid crystal comprising mixed ester liquid crystal in combination with a miscible dopant of the foregoing type.

Further objects and features of the invention will be apparent from the following description in which the preferred embodiments have been set forth in detail.

In accordance with the above objects, a novel optically active chiral nematic compound useful for reducing the response time of mixed esters liquid crystals has been formed of the formula:

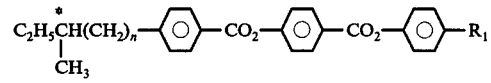

wherein $n$ varies from 1-5, and $R_1$ is a radical selected from the group consisting of an n-alkyl group, an n-alkoxy group, an n-acyloxy group, an n-alkyl carbonato group, a cyano group, and a nitro group, and the (*) signifies that the compound is optically active. The cyano and nitro group containing compounds are preferred because they provide the lowest operating voltage, e.g., on the order of 1.5 volts, to a liquid crystal display.

A novel nematic mixed ester liquid crystal composition with good temperature range and suitable for a field effect liquid crystal display includes (a) a mixture of alkylphenyl benzoates comprising:

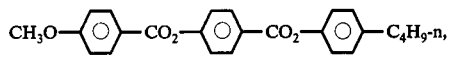

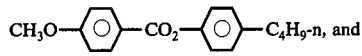

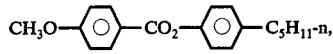

and (b) a mixture of cyanophenyl benzoates of the formula:

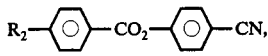

wherein $R_2$ is selected from the group of n-alkyl radicals, n-alkoxy radicals, and n-alkyl carbonato radicals.

BRIEF DESCRIPTION OF THE DRAWINGS

FIGS. 1 and 2 are phase diagrams of mixed ester compositions in accordance with the present invention.

FIGS. 3 and 4 are plots of comparative response times with and without the dopant of the present invention.

DETAILED DESCRIPTION OF THE PREFERRED EMBODIMENTS

In accordance with the present invention, novel optically active liquid crystal compositions are provided for use in an electro-optical display. Such liquid crystals are twisted in a field effect display to be described hereinafter.

CHIRAL NEMATIC COMPOUND

In conventional liquid crystal compositions, the twist alignment is imparted to the ester mixtures by alignment of the boundary layer as set forth below. Without such aligned areas, there would be no tendency for the esters to shift from a homeotropic to a twist mode.

In accordance with one embodiment of the invention, a chiral nematic compound (herein "the dopant") is formed to impart a twist memory to the ester mixtures. The dopant is characterized by the following formula:

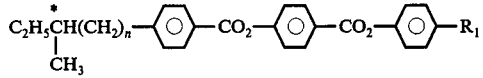

wherein $n$ varies from 1–5, and $R_1$ is a radical selected from the group consisting of an n-alkyl group, an n-alkoxy group, an n-acyloxy group, an n-alkyl carbonato group, a cyano group, and a nitro group. Where $R_1$ contains an alkyl group, it includes from 1 to 8 carbon atoms.

PROCEDURE 1

In the embodiment in which $R_1$ is a normal alkyl group including from 1–8 carbon atoms, and $n = 1$, the dopant is suitably formed by the reaction of (+)-4-β-methylbutylbenzoyl chloride,

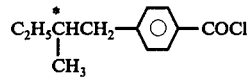

and 4-n-alkylphenyl-4'-hydroxybenzoate,

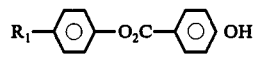

wherein $R_1$ are defined as above.

The (+)-4-β-methylbutylbenzoyl chloride of this invention is prepared by starting with (−)-2-methylbutan-1-ol according to the following procedure:

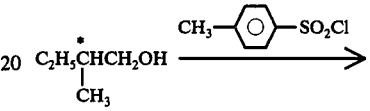  (1)

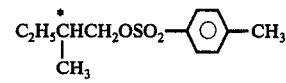  (2)

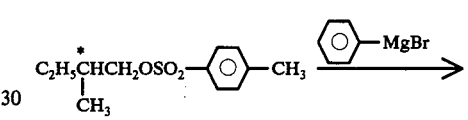

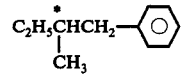  (3)

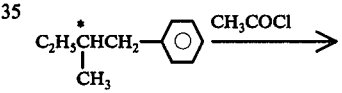

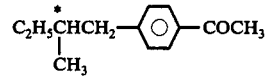  (4)

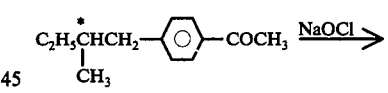

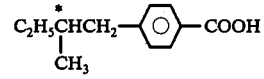  (5)

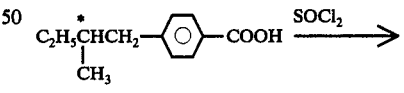

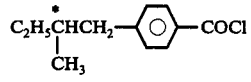

The 4n-alkylphenyl-4'-hydroxybenzoates of this invention are prepared by the reaction of 4-hydroxybenzoic acid and an appropriate 4-n-alkylphenol. The commercially unavailable 4-n-alkylphenols are prepared from the corresponding 4-n-alkylanilines. The preparing procedure are exemplified with 4-n-butylphenyl-4'-hydroxybenzoate as follows:

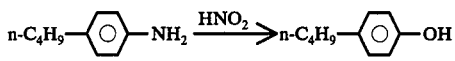  (6)

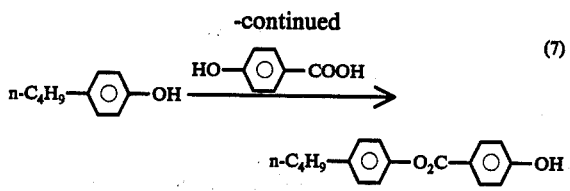

(7)

The (+)-4-n-alkylphenyl-4'-(4-β-methylbutylbenzoyloxy)-benzoates benzoates of this invention are prepared by the reaction of (+)-4-β-methylbutylbenzoyl chloride and an appropriate 4-n-alkylphenyl-4'-hydroxybenzoate. The preparing procedure is exemplified with (+)-4-n-butylphenyl-4'-(4-β-methylbutylbenzoyloxy)-benzoate as follows:

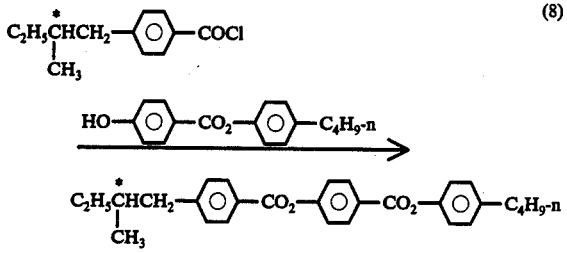

(8)

PROCEDURE 2

In the formulation of the dopant wherein $n = 1$ and $R_1$ is an alkoxy group (-OR), the procedure to form (+)-4-n-alkyloxyphenyl-4'-(4-β-methylbutylbenzoyloxy)-benzoate is as follows:

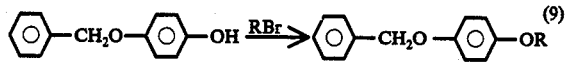
(9)

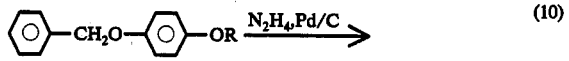
(10)

(11)

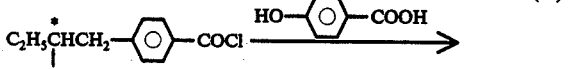
(12)

(13)

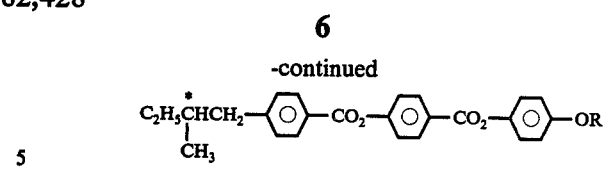

It is noted that the reaction products of equations (11) and (12) are believed to be novel intermediates particularly suited to form the product of equation (13). The precise reaction conditions for the alternate procedure of equations (9) – (13) are analogous to those of equations (1) – (8). For example the conditions for the reaction of equation (13) may be derived by reference to conditions set forth with respect to the analogous reaction (8).

PROCEDURE 3

This is an alternate procedure for forming the final chiral nematic product of Procedure 2.

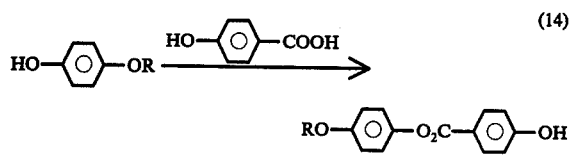
(14)

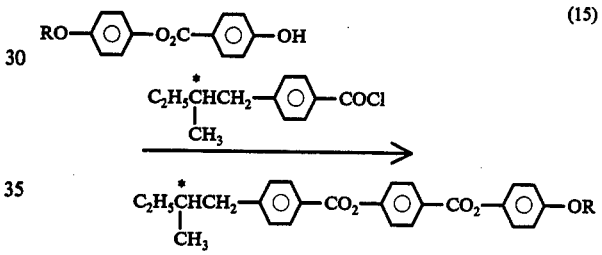
(15)

The reactions of equations (14) and (15) are analogous to the reactions of equations (7) and (8), respectively. Thus, appropriate modifications may be made to the reaction conditions of the latter equations, set forth above.

PROCEDURE 4

In the formulation of the dopant wherein $R_1$ is an n-acyloxy group (—OCOR), and n = 1, the procedure to form (+)-4-n-acyloxyphenyl-4'-(4-β-methylbutylbenzoyloxy)-benzoate is as follows:

(16)

(17)

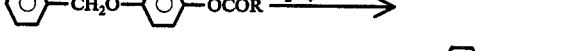

(18)

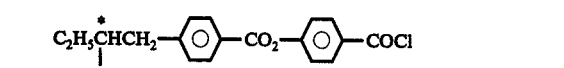

-continued $$C_2H_5\overset{*}{C}HCH_2-\langle O \rangle-CO_2-\langle O \rangle-CO_2-\langle O \rangle-OCOR$$

The reactions of equations (16), (17), and (18) are analogous to the reactions of equations (9), (10), and (8), respectively, which may be referred to for appropriate reaction conditions.

PROCEDURE 5

In the formulation of the dopant wherein $R_1$ is an n-alkyl carbonato group ($-OCO_2R$), and n = 1, the procedure to form (+)-4-n-alkyloxycarbonyloxyphenyl-4'-(4-β-methylbutylbenzoyloxy)-benzoate is as follows:

$$\langle O \rangle-CH_2O-\langle O \rangle-OH \xrightarrow{ROCOCl} \quad (19)$$

$$\langle O \rangle-CH_2O-\langle O \rangle-OCO_2R$$

$$\langle O \rangle-CH_2O-\langle O \rangle-OCO_2R \xrightarrow{N_2H_4, Pd/C} \quad (20)$$

$$HO-\langle O \rangle-OCO_2R \quad (21)$$

$$HO-\langle O \rangle-OCO_2R$$

$$C_2H_5\overset{*}{C}HCH_2-\langle O \rangle-CO_2-\langle O \rangle-COCl \longrightarrow$$

$$C_2H_5\overset{*}{C}HCH_2-\langle O \rangle-CO_2-\langle O \rangle-CO_2-\langle O \rangle-OCO_2R$$

Equations (19), (20), and (21) are analogous to equations (9), (10), and (8), respectively.

PROCEDURE 6

In the formulation of dopant wherein $R_1$ is either a cyano ($-CN$) or a nitro group ($-NO_2$), and n = 1, the following series of reactions may be employed for synthesis of (+)-4-cyanophenyl-4'-(4-β-methylbutylbenzoyloxy)-benzoate or (+)-4-nitrophenyl-4'-(4-β-methylbutylbenzoyloxy)-benzoate is as follows:

$$C_2H_5\overset{*}{C}HCH_2-\langle O \rangle-COCl \xrightarrow{HO-\langle O \rangle-COOH} \quad (22)$$

$$C_2H_5\overset{*}{C}HCH_2-\langle O \rangle-CO_2-\langle O \rangle-COOH$$

$$C_2H_5\overset{*}{C}HCH_2-\langle O \rangle-CO_2-\langle O \rangle-COOH \xrightarrow{SOCl_2} \quad (23)$$

$$C_2H_5\overset{*}{C}HCH_2-\langle O \rangle-CO_2-\langle O \rangle-COCl$$

$$C_2H_5\overset{*}{C}HCH_2-\langle O \rangle-CO_2-\langle O \rangle-COCl \quad (24)$$

$$\xrightarrow{HO-\langle O \rangle-CN \text{ (or } HO-\langle O \rangle-NO_2)}$$

$$C_2H_5\overset{*}{C}HCH_2-\langle O \rangle-CO_2-\langle O \rangle-CO_2-\langle O \rangle-CN \text{ (NO}_2)$$

PROCEDURE 7

In the formulation of the dopant wherein n = 2 or more, and $R_1$ is a radical selected from the group consisting of an n-alkyl group, an n-alkoxy group, an n-acyloxy group, or an n-alkyl carbonato group, the following procedure may be employed:

$$C_2H_5\overset{*}{C}HCH_2OSO_2-\langle O \rangle-CH_3 \quad (25)$$

$$\xrightarrow{\langle O \rangle-(CH_2)_m MgBr, \ m = 1, 2, 3, 4} C_2H_5\overset{*}{C}H(CH_2)_n-\langle O \rangle$$

$$C_2H_5\overset{*}{C}H(CH_2)_n-\langle O \rangle \xrightarrow{CH_3COCl} \quad (26)$$

$$C_2H_5\overset{*}{C}H(CH_2)_n-\langle O \rangle-COCH_3$$

$$C_2H_5\overset{*}{C}H(CH_2)_n-\langle O \rangle-COCH_3 \xrightarrow{NaOCl} \quad (27)$$

$$C_2H_5\overset{*}{C}H(CH_2)_n-\langle O \rangle-COOH$$

$$C_2H_5\overset{*}{C}H(CH_2)_n-\langle O \rangle-COOH \xrightarrow{SOCl_2} \quad (28)$$

$$C_2H_5\overset{*}{C}H(CH_2)_n-\langle O \rangle-COCl$$

$$C_2H_5\overset{*}{C}H(CH_2)_n-\langle O \rangle-COCl \quad (29)$$

$$\xrightarrow{HO-\langle O \rangle-CO_2-\langle O \rangle-R_1}$$

$$C_2H_5\overset{*}{C}H(CH_2)_n-\langle O \rangle-CO_2-\langle O \rangle-CO_2-\langle O \rangle-R_1$$

Equations (25), (26), (27), (28), and (29) are analogous to equations (2), (3), (4), (5), and (8), respectively.

PROCEDURE 8

In the formulation of dopant wherein n = 2 or more, and $R_1$ is a cyano or nitro group, the alternative procedure may be as follows:

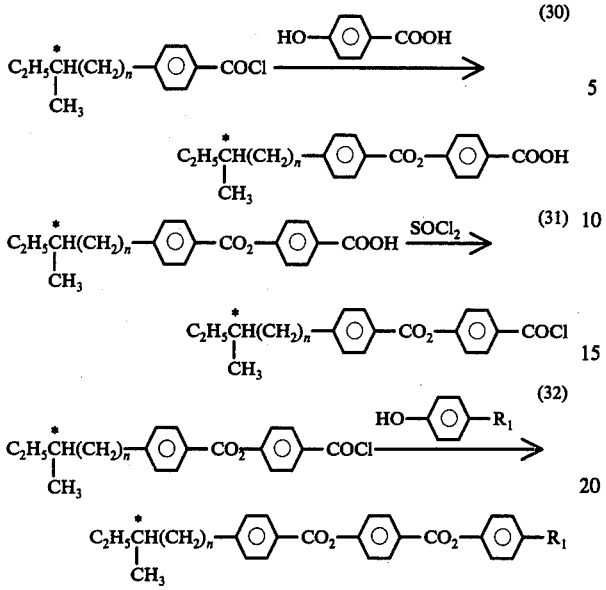

Equations (30), (31), and (32) are analogous to equations (11), (12), and (8), respectively.

In view of the foregoing, it is apparent that there are two general methods for forming the chiral nematic compound of the present invention. One technique is exemplified by the last step of procedure 1, [Equation (8)]. The other technique is exemplified by the last step of procedure 2, [Equation (13)].

Each of the foregoing compounds is optically active because of the asymmetric branch chained methyl butyl portion of the compound. This dopant is characterized by a tight optical pitch to its spiral structure. The addition of dopant to an ester mixture causes the mixture to become chiral nematic. By careful selection of the dopant concentration, the pitch of the ester mixture will be the desired four times the cell spacing so that the imparted pitch of the ester mixture matches the pitch induced by the treatment of the interior surfaces of the cell as explained hereinafter. Because of this induced twist, it has been found that the addition of relatively minor amounts of this material to ester mixtures produces a twist nematic display with a significantly improved response time. Depending upon the spacing between the electrodes, effective amounts of the foregoing dopant for this purpose comprise on the order of 0.2 to 2 weight percent, and more commonly 0.4 to 1 weight percent of the total liquid crystal composition. At these low percentages, the dopant does not significantly affect the temperature range or dielectric anisotropy of the mixed ester composition.

The following tables summarize the phase transition temperatures of chiral nematic dopants according to the invention, wherein $R_1$ is a normal alkyl group as set forth in the table varying from 1-8 carbon atoms.

Table II-A (n= 1)

$C_2H_5\overset{*}{C}HCH_2$—〇—$CO_2$—〇—$CO_2$—〇—$R_1$
|
$CH_3$

| $R_1$ | Mesomorphic Range (° C) | |
|---|---|---|
| | K—CH* | Ch—I** |
| $C_1$ | 90 – 91 | 164.8 |
| $C_2$ | 78 – 79 | 154.2 |

Table II-A-continued (n= 1)

$C_2H_5\overset{*}{C}HCH_2$—〇—$CO_2$—〇—$CO_2$—〇—$R_1$
|
$CH_3$

| $R_1$ | Mesomorphic Range (° C) | |
|---|---|---|
| | K—CH* | Ch—I** |
| $C_3$ | 80.8 – 81.2 | 162.4 |
| $C_4$ | 77.2 – 77.4 | 152 |
| $C_5$ | 67.5 – 68 | 152.7 |
| $C_6$ | 76.7 – 77.7 | 145 |
| $C_7$ | 76.4 – 77.0 | 140.8 |
| $C_8$ | 72.6 – 73.4 | 154.3 |
| CN | 103 – 103.6 | 192 |
| $NO_2$ | 131 – 132 | 205 |

Table II-B (n = 2)

$C_2H_5\overset{*}{C}H\ C_2H_4$—〇—$CO_2$—〇—$CO_2$—〇—$R_1$
|
$CH_3$

| $R_1$ | Mesomorphic Range (° C) | |
|---|---|---|
| | K—Ch | Ch—I |
| $CH_3$ | 109 – 109.7 | 158.1 |
| $C_2H_5$ | 103.8 – 104.5 | 147.5 |
| $C_3H_7$ | 96.6 – 97.2 | 158 |
| $C_4H_9$ | 85.0 – 85.7 | 145.9 |
| $C_5H_{11}$ | 78.5 – 79.6 | 148.6 |
| $C_6H_{13}$ | 73 – 74 | 145.5 |
| $C_7H_{15}$ | 77.6 – 78.6 | 146.9 |
| $C_8H_{17}$ | 80 – 81 | 137.1 |

Table II-C (n = 3)

$C_2H_5\overset{*}{C}H\ C_3H_6$—〇—$CO_2$—〇—$CO_2$—〇—$R_1$
|
$CH_3$

| $R_1$ | Mesomorphic Range (° C) | |
|---|---|---|
| | K—Ch | Ch—I |
| $CH_3$ | 90.7 – 91.7 | 148.5 |
| $C_2H_5$ | 91.5 – 92.5 | 145 |
| $C_3H_7$ | 73 – 74.5 | 150.9 |
| $C_4H_9$ | 78 – 79.5 | 140 |
| $C_5H_{11}$ | 68.7 – 69.5 | 140.5 |
| $C_6H_{13}$ | 73.5 – 74.3 | 141.5 |
| $C_7H_{15}$ | 77 – 78 | 144.2 |
| $C_8H_{17}$ | 74.7 – 75.7 | 137 |

*K—Ch: crystal to chiral nematic transition
**Ch—I: chiral nematic to isotropic transition The above novel dopant has a number of important characteristics. Because of its tight pitch, relatively small amounts of it serve to provide a natural twist to ester mixtures to decrease the response time. Also, it was formulated to be highly miscible with a wide variety of ester mixtures. Variance of the amount of dopant employed correspondingly varies the pitch of the overall liquid crystal composition as described above. Therefore, the requisite cell spacing for a 90° twist can be varied within a wide range by varying the concentration of dopant. Thus, it may be possible to use wider spacing for an ester mixture than is presently available. This avoids fabrication problems inherent in tight spacing presently employed in undoped liquid crystal materials.

It has been found that when $R_1$ of the novel dopant is substituted with a strong electron-withdrawing (cyano) group, and the dopant is added to a mixed ester liquid crystal composition, the operating voltage of the liquid crystal in a display is significantly reduced. For example, the operating voltage of a mixed ester composition including the dopant of Table II-A with $R_1 = C_1 - C_8$ at a concentration of 0.6 weight percent dopant and a cell spacing of 11-12μ is on the order of 6.0 volts. (see Table XI, infra). By substituting dopant with $R_1 = CN$, an operating voltage of 1.5 volts is sufficient with excellent response times.

It is known that the nitro group is of comparable electron-withdrawing capability with the foregoing cyano group. For example, the electro-withdrawing electric moment of the cyano and nitro derivatives of benzene are 4.4 and 4.3, respectively.

MIXED ESTER LIQUID CRYSTAL COMPOSITION

The foregoing novel dopant material is extremely useful to impart a twist characteristic to a mixed ester composition employed as a liquid crystal in an electro-optical display. This speeds up the response time to an electric field, a particularly important feature at higher voltages where response times of such ester mixtures without dopant are very slow.

A novel mixed ester composition has been developed which is particularly suitable for mixture with the above dopant to form a liquid crystal having excellent response times, nematic temperature range, a highly positive dielectric anisotropy, and good contrast ratios. This liquid crystal composition, having a nematic temperature range of at least 0° to 50° C comprises (a) a mixture of alkylphenyl benzoates comprising:

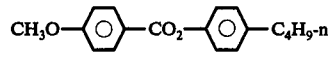

and (b) a mixture of cyanophenyl benzoates of the formula:

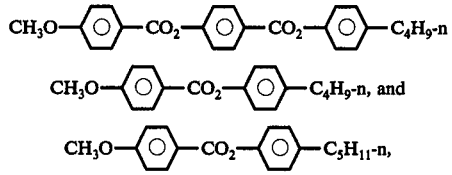

wherein $R_2$ is selected from the group of n-alkyl radicals, n-alkoxy radicals, and n-alkyl carbonato radicals.

The alkyl benzoates of part (a) of the mixture are selected to provide an extremely wide temperature range. However, such materials have a negative or weak positive dielectric anistropy. Thus, the cyano benzoate components of the mixture set forth in part (b) provide a strong positive anisotropy to the overall mixture. However, such materials do not have a sufficiently broad temperature range. By carefully selecting combinations of alkyl benzoate mixtures and cyano benzoate mixtures, components (a) and (b) are miscible in each other, an important feature of the invention. It has been found to be important to employ at least the foregoing three alkyl benzoates together with at least two cyano benzoates of the foregoing formula to optimize the temperature range and response time.

Other alkylphenyl benzoates which can be added to the above ester mixtures to further increase the mixture temperature range include the following:

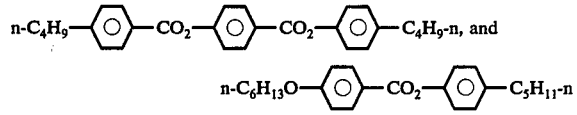

Examples of negative or weak positive anisotropic alkyl esters which are particularly effective in forming composition (a) of the above mixture for excellent nematic temperature ranges are as follows:

Table III

| Compound | Structure | Name |
| --- | --- | --- |
| 1 | 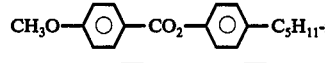 | 4-n-butylphenyl-4'-methoxybenzoate |
| 2 | 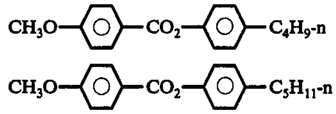 | 4-n-pentylphenyl-4'-methoxybenzoate |
| 3 | 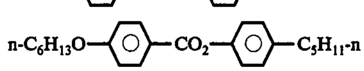 | 4-n-pentylphenyl-4'-n-hexyloxybenzoate |
| 4 | 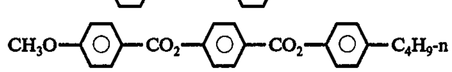 | 4-n-butylphenyl-4'-(4-methoxybenzoyloxy)-benzoate |
| 5 | 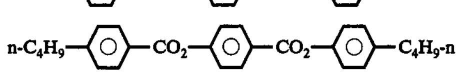 | 4-n-butylphenyl-4'-(4-n-butylbenzoyloxy)-benzoate |

For simplicity of description, where tabulated, these compounds will be referred to hereinafter by the numbers to the left of the table.

The following tables illustrate the mesomorphic temperature range for compositions including two different sets of four of the above five compounds.

Table IV

| Composition No. | Compound and Weight Percent | | | | Mesomorphic Range °C | |
| --- | --- | --- | --- | --- | --- | --- |
| | 1 | 2 | 3 | 4 | KN* | NI** |
| 1 | 25.5 | 38.3 | 21.2 | 15.0 | −8 | 58.5 |
| 2 | 15.9 | 47.8 | 21.3 | 15.0 | −4 | 60.5 |
| 3 | 27.0 | 40.5 | 22.5 | 10.0 | +1 | 52.5 |
| 4 | 18.9 | 44.1 | 27.0 | 10.0 | −1 | 53.5 |
| 5 | 19.2 | 44.6 | 21.2 | 15.0 | −6 | 59.0 |
| 6 | 23.8 | 35.7 | 25.5 | 15.0 | −4 | 59.0 |
| 7 | 24.0 | 36.0 | 20.0 | 20 | +8 | 64.0 |
| 8 | 22.4 | 33.6 | 24.0 | 20 | +9 | 64.5 |

*KN : Transition from the crystalline to nematic phase
**NI : Transition from the nematic to isotropic phase Table V

| Composition No. | Compound and Weight Percent | | | | Mesomorphic Range °C | |
| --- | --- | --- | --- | --- | --- | --- |
| | 1 | 2 | 4 | 5 | KN | NI |
| 9 | 28 | 42 | 15 | 15 | −10 | 78 |
| 10 | 24 | 36 | 20 | 20 | −4 | 88.5 |
| 11 | 26 | 39 | 17.5 | 17.5 | −6 | 82 |

Table V-continued

| Composition No. | Compound and Weight Percent | | | | Mesomorphic Range °C | |
|---|---|---|---|---|---|---|
| | 1 | 2 | 4 | 5 | KN | NI |
| 12 | 21 | 49 | 12 | 18 | −4 | 76 |
| 13 | 17.5 | 52.5 | 9 | 21 | 2 | 76.5 |
| 14 | 32 | 48 | 10 | 10 | −3 | 62 |
| 15 | 24 | 56 | 8 | 12 | +2 | 61 |
| 16 | 20 | 60 | 6 | 14 | +5 | 62 |

A composition corresponding to the four components of Table III is as follows:

Table VI

| Compound | Weight Percent |
|---|---|
| 1 | 25+ ± 10 |
| 2 | 38 ± 8 |
| 3 | 24 ± 5 |
| 4 | 15 ± 5 |

A composition corresponding to the four components of Table IV is as follows:

Table VII

| Compound | Weight Percent |
|---|---|
| 1 | 25 ± 10 |
| 2 | 50 ± 15 |
| 4 | 15 ± 10 |
| 5 | 15 ± 7 |

A composition of alkyl benzoates which encompasses the range of the three common components in Tables III and IV which form the predominant portion of the alkyl benzoate component is as follows:

Table VIII

| Compound | Weight Percent |
|---|---|
| 1 | 26 ± 10 |
| 2 | 40 ± 15 |
| 4 | 15 ± 7 |

As set forth above, the cyano benzoate component of the liquid crystal is included because of its positive dielectric anisotropy. The ones of the present invention are characterized by a relatively wide temperature range and miscibility in the above alkylphenyl benzoates. Many different cyanophenyl benzoates are encompassed by the foregoing formula

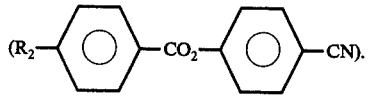

It is preferable that at least two compounds of the cyanophenyl benzoate formula includes at least two and as many as three or more different n-alkyl groups as component $R_2$. In addition, an n-alkyl carbonato group is preferably employed as the $R_2$ component of one of cyanophenyl benzoate components. This mixture is particularly effective because of its relatively wide temperature range and high positive dielectric anisotropy. A specific formulation of the cyanophenyl benzoate component because of their wide temperature range and high miscibility with the foregoing alkylphenyl benzoates are as follows:

Table IX

| Composition | Cyano Benzoates Component and Weight Percent | | | | Mesomorphic Range °C | |
|---|---|---|---|---|---|---|
| | * | ** | *** | **** | KN | NI |
| A | 60 | 22 | 8 | 10 | 4–5 | 53.6 |
| B | 56 | 25 | 10 | 9 | 6–7 | 54 |
| C | 53 | 22 | 13 | 12 | 7–8 | 54.5 |
| D | 51 | 17 | 20 | 12 | 12–13 | 56.8 |
| E | 46 | 11 | 27 | 16 | 17 | 58.3 | wherein:

* is 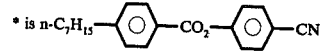

** is 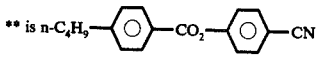

*** is 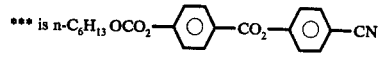

**** is 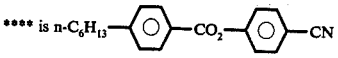

Referring to FIGS. 1 and 2 a phase diagram is illustrated of preferred alkylphenyl benzoate compositions A and C in varying proportions with corresponding preferred cyanophenyl benzoates of composition B. In each instance, a minimum of 15 weight percent of the alkylphenyl benzoate is necessary for a lower transition temperature of 0° C or below.

It has been found in general that at least 30 weight percent of the cyanophenyl benzoates in the above mixtures can be employed at an operating voltage below 1.5 volts. Mixtures containing from 10 to 30 weight percent cyanophenyl benzoates are suitable for operable voltages above 1.5 volts.

MIXED ESTERS WITH AND WITHOUT DOPANT

Many of the foregoing ester mixtures are characterized by excellent temperature ranges and contrast ratios. It has been found that they may be employed at relatively low voltages, e.g., 1.5 volts, in certain electro-optical displays without excessively slow response times. Thus, such mixtures are useful at low voltages without a dopant. At high voltages, the contrast ratio of undoped ester mixtures tend to bounce or rise after the commencement of decay.

In a liquid crystal display, it is conventional for the time for the contrast ratio to rise to a maximum in response to an electric field and to fall to its original value to be in a general bell-shaped curve. Conventional terminology employed in the liquid crystal display field is as follows:

$I_{DR}$ — the time required for the contrast ratio to reach 10% of its maximum intensity;

$T_R$ — the time for the contrast ratio to rise from 10% to 90% of its maximum intensity;

$T_{DF}$ — the time for the contrast ratio to fall to 90% of its maximum intensity; and $T_F$ — the time for the contrast ratio to fall from 90% to 10% of its maximum intensity. It is important that the total of $T_{DR}$, $T_R$, $T_{DF}$ and $T_F$ be less than 600 milliseconds for optimum liquid crystal response. It is also preferable that the total of $T_{DF}$ and $T_F$ be 300 milliseconds or less.

Addition of the dopant of the present invention decreases the response time for a mixed ester display and eliminates any bounce in the contrast ratio.

The advantages of adding dopant to a liquid crystal system to decrease response time is apparent from the following Tables (X and XI). The display of Table X includes a liquid crystal composition of 25 weight percent "A" and 75 weight percent "B" as defined in FIG. 1. This composition was filled into a watch-type digital display with a narrow cell spacing (7.1 - 7.4μ) in which the final treatment of the inner cell walls was by slope deposition of silicon monoxide at a low angle. In Table X, the response time of this composition without dopant is compared to the response time with 0.6 weight percent dopant of the foregoing formula wherein $n = 1$, and $R_1$ is an n-alkyl group varying from 1-8 carbon atoms. The display was actuated at 3 volts.

Table X

| Dopants | Response Time (ms) | | | |
|---|---|---|---|---|
| | $T_{DR}$ | $T_R$ | $T_{DF}$ | $T_F$ |
| 0 | 21 | 38 | 123 | 119 |
| $C_1$ | 22 | 35 | 79 | 84 |
| $C_2$ | 25 | 31 | 77 | 86 |
| $C_3$ | 23 | 36 | 79 | 89 |
| $C_4$ | 22 | 48 | 82 | 91 |
| $C_5$ | 22 | 36 | 71 | 82 |
| $C_6$ | 25 | 31 | 83 | 84 |
| $C_7$ | 21 | 36 | 83 | 88 |
| $C_8$ | 22 | 36 | 90 | 89 |

It is apparent that although the response time is relatively fast for ester mixtures without dopant there is a substantial improvement in the presence of dopant.

Referring to Table XI, a liquid crystal composition of 75 weight percent "B" and 25 weight percent "C" as defined in FIG. 2 was employed in a watch-type digital display with the same cell wall treatment as in Table X but at a wide cell spacing (11–12μ). The response time of this composition without dopant is compared to the response time with 0.8 weight percent dopant of the foregoing formula wherein $n = 1$ and $R_1$ is an n-alkyl group varying from 1-8 carbon atoms. The operating voltage was 6 volts.

Table XI

| Dopants | Response Time (ms) | | | |
|---|---|---|---|---|
| | $T_{DR}$ | $T_R$ | $T_{DF}$ | $T_F$ |
| 0 | 30 | 215 | 185 | 265 |
| $C_1$ | 25 | 205 | 60 | 220 |
| $C_2$ | 40 | 190 | 130 | 195 |
| $C_3$ | 30 | 220 | 115 | 185 |
| $C_4$ | 25 | 230 | 100 | 225 |
| $C_5$ | 35 | 225 | 130 | 190 |
| $C_6$ | 30 | 190 | 110 | 210 |
| $C_7$ | 25 | 210 | 40 | 250 |
| $C_8$ | 20 | 230 | 40 | 240 |

It is apparent that the response time without dopant for this relatively high voltage was slow. FIG. 3, a plot of percent absorbance versus time, illustrates this slow response time as well as undesirable "bounce" upon turning the switch to an "off" switch.

FIG. 4 is a plot of response time for the same liquid crystal composition to which 0.8 weight percent dopant (n=1, $R_1$ = $C_1$) has been added. The response time after turning off the current is significantly faster and the "bounce" has been eliminated.

There are significant fabrication advantages in using large cell spacing (e.g. 11–12μ) for a liquid crystal display. One disadvantage is the required use of voltages on the order of 6V with a dopant in which $R_1 = C_1 - C_8$ to decrease response time. Where $R_1$ = CN or $NO_2$, operating voltage may be decreased to 1.5V with excellent response times. See Table XII below.

Table XII

| Dopant | Concentration | Response time (ms) | | | |
|---|---|---|---|---|---|
| | | $T_{DR}$ | $T_R$ | $T_{DF}$ | $T_F$ |
| CN | 0.4 wt. % | 50 | 240 | 40 | 230 |

THE FIELD EFFECT LIQUID CRYSTAL DISPLAY

To form a typical electro-optical display in accordance with the present invention, a very thin film of liquid crystal material is placed between two transparent electrodes. The outer surfaces of the two electrodes are covered with polarizers which are orthogonal to each other. The liquid crystal molecules at the inner surface of each electrode are aligned parallel to the polarizer for that electrode. Since the polarizers are orthogonal with respect to each other, the film of liquid crystal is in the form of a 90° twist from the inner surface of one electrode to the inner surface of the other electrode. A reflector is placed against the polarizer of the second electrode.

Unpolarized light is linearly polarized in the Y-direction by the first polarizer. This linearly polarized light followed the 90° twist as it passes through the liquid crystal and arrives properly in the X-direction, parallel to the second polarizer. After passing through the second polarizer, the light is now reflected back through the liquid crystal material, following the 90° twist, arriving aligned in a Y-direction and will pass out through the first polarizer. To an observer, the display looks clear bright.

When an electric field is applied across the two electrodes, the liquid crystal molecules align themselves with the field. The molecules "stand up" almost 90° to the surface of the electrodes and polarizers, except at the boundary layer. Unpolarized light is linearly polarized in a Y-direction by the first polarizer. This linearly polarized light now passes through the field aligned liquid crystal film without changing its Y-direction polarization, and is absorbed by the X-direction polarizer. To an observer, the display looks black due to the absence of reflected light. When the electric field is removed, the liquid crystal film resumes its 90° twist configuration.

In an alternative embodiment, if the polarizers are oriented parallel with each other, the display appears black without an electric field and clear bright when an electric field is applied. The most common choice is the use of dark digits on a light background. Therefore, the polarizers are normally aligned 90° to each other.

The construction of electro-optical displays of the foregoing type are well known. Different techniques may be employed to provide proper molecular alignment of the liquid crystal material. One technique is angular evaporation of silicon monoxide. It is evaporated onto the inner surface of each glass plate at a typical angle of 85° from the surface normal. Another technique is the use of a surfactant which is carefully applied by a simple mechanical single-stroke polishing action in one direction.

In order to more clearly illustrate the present invention, the following example of a method of formation of the chiral nematic dopant in which $n = 1$ and $R_1$ is an n-butyl group is illustrated.

EXAMPLE 1

Formation of (+)-β-methylbutyl-4-toluenesulfonate (Eq. (1) above).

4-toluenesulfonyl chloride (381g, 2m) was added in portion to a stirred solution of (−)-2-methylbutane-1-ol (88.15g, 1m) $[\alpha]_D^{25}$ = 4.61 (neat) in pyridine (900ml) at 0°–5° C. The reaction was stirred for an additional half an hour and left overnight in the refrigerator. The reaction mixture was diluted with an excess of water, stirred for two hours in an ice bath, and extracted with ether (4×250ml). The ether extract was washed with cold 6N hydrochloric acid until all the pyridine has been removed, then with water, and the organic layer dried over sodium sulfate and potassium carbonate. The solvent was stripped and the residue was vacuum distilled to give (+)-β-methyl-4-toluenesulfonate (227g, 93.4%) bp 133°–138° C/2.27mm.

EXAMPLE 2

Formation of (+)-β-methylbutylbenzene (Eq. (2) above).

Phenylmagnesium bromide-ether solution was prepared from bromobenzene (64.5g, 0.41m), magnesium turnings (9.85g, 0.41m), and anhydrous ether (500ml). The reagent was cooled and (+)-β-methylbutyl-4-toluenesulfonate (200g, 0.82m) in ether (800ml) was added in drops. When the addition was complete, the reaction mixture was stirred for two hours, refluxed for two hours and left to stand overnight. Aqueous sulfuric acid was added until a clear solution was formed. The layers were separated. The aqueous layer was extracted with ether (3×250ml), and the combined organic layers were washed with sodium bicarbonate solution, water and dried over anhydrous sodium sulfate. The solvent was evaporated and the residue was steam-distilled. Fractional distillation of the crude product at reduced pressure yielded (+)-β-methylbutylbenzene (38.7g, 64.8%), bp. 74°–77° C at 12 mm pressure.

EXAMPLE 3

Formation of (+)-4-β-methylbutylacetophenone (Eq. (3) above).

(+)-β-mthylbutylbenzene (36g, 0.24m) was added to a stirred solution of acetyle chloride (24g, 0.31m) and aluminum chloride (48g, 0.36m) in carbon tetrachloride (185ml) at 0°–5° C. Stirring was continued for two hours and the resulting reaction mixture was poured into a mixture of concentrated hydrochloric acid (130ml) and ice (260g). The organic layer was washed with 2N hydrochloric acid (2×130ml), saturated sodium bicarbonate solution (130ml) and finally with water and dried over anhydrous sodium sulfate. The solvent was stripped and the residue was vacuum-distilled to yield (+)-4-β-methylbutylacetophenone (38g, 83%) bp 93°–94° C at 0.2mm.

EXAMPLE 4

Formation of (+)-4-β-methylbutylbenzoic acid (Eq. (4) above).

Chlorine gas was passed into a stirred solution of sodium hydroxide (55g, 1.37m) in water (435ml) kept below 0° C until the solution was neutral to litmus. A solution of sodium hydroxide (10g) in water (15ml) was added. (+)-4-methylbutylbenzophenone (27.5g, 0.145m) was added in drops to the solution at 70°–85° C with stirring. Stirring was continued for an additional hour. The excess sodium hypochlorite was destroyed by adding a solution of aqueous sodium bisulfate. After cooling to room temperature the reaction mixture was acidified with concentrated hydrochloric acid. The solid was collected and washed with water. The air dried crude product was crystallized from ethanol to yield (+)-4-β-methylbutylbenzoic acid (19g, 69%), mp. 134°–135° C.

EXAMPLE 5

Formation of (+)-4-β-methylbutylbenzoyl chloride (Eq. (5) above.

A mixture of (+)-4-β-methylbutylbenzoic acid (19g, 0.1m) and thionyl chloride (30ml) was refluxed for four hours. The excess thionyl chloride was distilled at ordinary pressure. The residue was distilled under vacuum to yield (+)-4-β-methylbutylbenzoyl chloride (19g, 91.5%), bp. 90°–96° C at 0.5–0.6 mm pressure.

EXAMPLE 6

Formation of 4-n-butylphenol (Eq. (6) above).

A cold solution of sodium nitrite (28.95g, 0.419m) in water (90ml) was added in drops to a mixture of 4-n-butylaniline (60g, 0.402m), concentrated sulfuric acid (135g) and water (300ml) at 0°–5° C with stirring. After completion of addition the excess nitrous acid was tested with potassium iodide starch paper, and destroyed by the addition of urea. The resulting cold diazonium salt solution was slowly added to a boiling solution of water (210ml), sulfuric acid (375g) and anhydrous sodium sulfate (285g). The resulting reaction mixture was steam distilled. The distillate was collected until it became clear and saturated by adding sodium chloride. The resulting solution was extracted with ether and the combined ether extract were dried over anhydrous sodium sulfate. The solvent was evaporated and the residue was vacuum distilled to yield 4-n-butylphenol (44g, 73.3%), bp 106° C at 4.6 mm.

EXAMPLE 7

Formation of 4-n-butylphenyl-4'-hydroxybenzoate (Eq. (7) above).

Phosphoryl chloride (5.83g, 0.038m) was added to a mixture of 4-hydroxybenzoic acid (13.8g, 0.1m) and 4-n-butylphenol (15g, 0.1m). The reaction mixture was heated at 75°–80° C with occasional swirling for four hours and then poured slowly with vigorous stirring into a solution of sodium carbonate (12g, 0.113m) in water (80ml). The precipitate was collected and washed with water (4×20ml). The etheral solution of the crude product was washed with sodium bicarbonate solution and water. The solvent was evaporated and the residue was recrystallized from carbon tetrachloride to yield 4-n-butylphenyl-4'-hydroxybenzoate (14.8g, 55%) mp 142°–144° C.

EXAMPLE 8

Formation of (+)-4-n-butylphenyl-4'-(4-β-methylbutylbenzoyloxy)-benzoate (Eq. (8) above).

A solution of (+)-4-β-methylbutylbenzoyl chloride (1.05g, 0.005m) in pyridine (4ml) was added to a stirred solution of 4-n-butylphenyl-4'-hydroxybenzoate (1.35g, 0.005m) in pyridine (6ml). After stirring for 8 hours the reaction mixture was acidified with diluted hydrochloric acid and extracted with ether. The combined etheral solution was washed with water, diluted sodium hydroxide and water, then dried over anhydrous sodium sulfate. The solvent was evaporated and the residue was recrystallized from ethanol to yield (+)-4-n-butylphenyl-4'-(4-β-methylbutylbenzoyloxy)-benzoate (1.5g, 67.5%) K-Ch 77.2°–77.4° C, Ch-I 152° C.

Examples 9–11 illustrate the formation of the novel dopant in which $R_1$ is a cyano group of the dopant in which n = 1.

EXAMPLE 9

Formation of (+)-4-(4'-β-methylbutylbenzoyloxybenzoic acid (Eq. (22) above).

A mixture of (+)-4-β-methylbutylbenzoyl chloride (8.4g, 0.04m) and 4-hydroxybenzoic acid (5.5g, 0.04m) in pyridine (60ml) was stirred at −5° C to 0° C for one hour. The reaction temperature was allowed to rise to room temperature and the reaction mixture was poured into a solution of concentrated hydrochloric acid (100ml) and water (100ml) at −10° C with stirring. Stirring was continued until the oily material was solidified. The solid was filtered and washed with 10% hydrochloric acid solution then with water. The air-dried crude product was crystallized from benzene to yield (+)-4-(4'-β-methylbutylbenzoyloxy)-benzoic acid (5.7g, 46%) K-Ch 168°–170° C, Ch-I 247° C.

EXAMPLE 10

Formation of (+)-4-(4'-β-methylbutylbenzoyloxy)-benzoyl chloride (Eq. (23) above).

A mixture of (+)-4-(4'-β-methylbutylbenzoyloxy)-benzoic acid (5.7g, 0.0182m) and thionyl chloride (20ml) was refluxed for four hours. The excess thionyl chloride was distilled and the residue was used in the following reaction without purification.

EXAMPLE 11

Formation of (+)-4-cyanophenyl-4'-(4-β-methylbutylbenzoyloxy)-benzoate (Eq. (24) above).

A solution of (+)-4(4'-β-methylbutylbenzoyloxy)-benzoyl chloride (residue from Example 10) and 4-hydroxybenzonitrile (2.13 g, 0.018m) in pyridine (20 ml) was stirred for 8 hours. The reaction mixture was acidified with diluted hydrochloric acid and extracted with ether. The combined etheral solution was washed with water, diluted sodium hydroxide and water, then dried over anhydrous sodium sulfate. The solvent was evaporated and the residue was recrystallized from ethanol to yield (+)-4-cyanophenyl-4'-(4-β-methylbutylbenzoyloxy)-benzoate (3.5 g, 47%) K-Ch 103°–103.6° C, Ch-I 192° C.

EXAMPLES 12–14

Formation of (+4)-4-nitropenyl-4'-(4-β-methylbutylbenzoyloxy)-benzoate (Eq. (22-24) above).

The procedures of Examples 9–11 were repeated with the substitution of 4-hydroxynitrobenzene for 4-hydroxybenzonitrile in Step 11.

What is claimed is:

1. In an electro-optical device including a field effect ester liquid crystal layer comprising p'-substituted-p-alkyl-and p-cyanophenylbenzoates, the improvement comprising from 0.2 to 2% of an optically active of chiral nematic compound in said liquid crystal layen, said optically active chiral nematic compound having the formula:

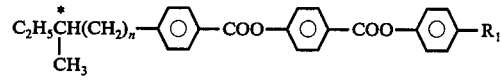

wherein n varies from 1–5, and $R_1$ is a radical selected from the group consisting of an n-alkyl group, an n-alkoxy group, an n-acyloxy group, an n-alkyl carbonato group, a cyano group, and a nitro group.

2. The electro-optical device of claim 1 in which $R_1$ is a normal saturated alkyl group including from 1-8 carbon atoms.

3. The electro-optical device of claim 1 in which $R_1$ is selected from the group consisting of cyano and nitro groups.

4. A nematic field-effect liquid crystal composition comprising a solution of:
   (a) at least one compound of the general formula:

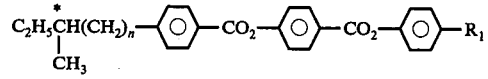

wherein n varies from 1–5, and $R_1$ is a radical selected from the group consisting of an n-alkyl group, an n-alkoxy group, an n-acyloxy group, an n-alkyl carbonato group, a cyano group, and a nitro group, and
   (b) a mixture of field effect esters miscible with compound (a) and having a nematic temperature range of at least 0° to 50° C and a positive dielectric anisotropy, said mixture of field-effect esters comprising a mixture of p'-substituted-p-alkyl-andp-cyanophenylbenzoates.

5. The composition of claim 4 in which mixture (b) comprise a plurality of different p'-substituted-p-cyanophenylbenzoate esters.

6. The composition of claim 4 in which mixture (b) comprises a plurality of p'-substituted-p-n-alkylphenylbenzoates and a plurality of p'-substituted-p-cyanophenylbenzoates.

7. The composition of claim 6 in which the compound of part (a) comprises from about 0.2 to 2 weight percent of the total composition.

8. The composition of claim 4 disposed in a liquid crystal layer between spaced facing transparent electrical conductors of an electro-optic device.

9. The composition of claim 8 in which the compound of part (a) is present in a concentration which imparts an approximately 90° twist to mixture (b) in the distance between said electrical conductors.

10. The composition of claim 4 in which $R_1$ is selected from the group consisting of cyano and nitro groups.

11. The composition of claim 4 having a nematic temperature range of 0° C to 50° C in which said ester mixture (b) comprises:

a mixture of p'-substituted-p-n-alkylphenylbenzoates comprising:

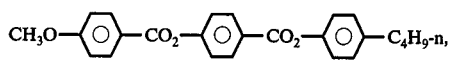

-continued

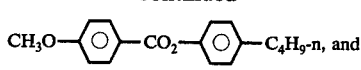, and

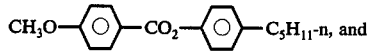, and a strongly positive anisotropic mixture of p'-substituted-p-cyanophenylbenzoates of the formula:

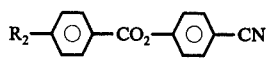

wherein $R_2$ is selected from the group of n-alkyl radicals, n-alkoxy radicals, and n-alkyl carbonato radicals.

12. The composition of claim 11 in which the p'-substituted-p-alkylphenyl-benzoate mixture comprises the major portion of the composition.

13. The composition of claim 11 in which the p'-substituted-p-alkylphenyl-benzoate mixture of also includes a minor amount of

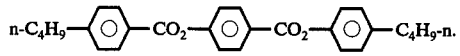

14. The composition of claim 11 in which the p'-substituted-p-alkylphenyl-benzoate mixture also includes a minor amount of

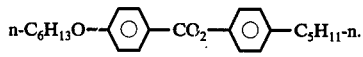

15. The composition of claim 11 in which the mixture includes at least two compounds of said p'-substituted-p-cyanophenylbenzoate formula in which $R_2$ is an n-alkyl group.

16. The composition of claim 11 in which the strongly positive anisotropic mixture of part (b) includes three compounds of said p'-substituted-p-cyanophenylbenzoate formula in which $R_2$ is an n-alkyl group, and one compound of said p'-substituted-p-cyanophenylbenzoate formula in which $R_2$ is an n-alkyl carbonato group.

17. The liquid crystal composition of claim 11 in which said p'-substituted-p-alkylphenylbenzoate mixture comprises:

| Compound | Weight % |
|---|---|
|  | 40 ± 15 |
|  | 26 ± 10 |
|  | 15 ± 7. |

18. The liquid crystal composition of claim 11 in which the p'-substituted-p-alkylphenylbenzoate mixture comprises:

| Compound | Weight % |
|---|---|
|  | 38 ± 8 |
|  | 25 ± 10 |
|  | 15 ± 5 |
|  | 24 ± 5. |

19. The liquid crystal composition of claim 11 in which the p'-substituted-p-alkylphenylbenzoate mixture comprises:

| Compound | Weight % |
|---|---|
|  | 50 ± 15 |
|  | 25 ± 10 |
|  | 15 ± 10 |
|  | 15 ± 7. |

* * * * *